United States Patent [19]

Murphy et al.

[11] Patent Number: 6,117,904
[45] Date of Patent: Sep. 12, 2000

[54] TREATMENT OF PRURITUS

[76] Inventors: Donald M. Murphy, 507 Holly Ave.;
Edward R. Ahrens, 1910 Jefferson St.,
both of Madison, Wis. 53711

[21] Appl. No.: 09/389,837

[22] Filed: Sep. 3, 1999

[51] Int. Cl.$^7$ ................................................ A61K 31/225
[52] U.S. Cl. ............................................................ 514/547
[58] Field of Search ............................ 514/11, 169, 724,
514/705, 547; 424/401, 449; 112/184

[56] References Cited

U.S. PATENT DOCUMENTS

| | | |
|---|---|---|
| 3,070,497 | 12/1962 | Knight . |
| 3,091,241 | 5/1963 | Kellett . |
| 3,975,515 | 8/1976 | Wajaroff et al. . |
| 3,998,966 | 12/1976 | Fried et al. . |
| 4,055,653 | 10/1977 | Offermanns et al. . |
| 4,061,753 | 12/1977 | Bodor et al. ............................ 514/263 |
| 4,091,753 | 5/1978 | Johnson et al. ......................... 112/184 |
| 4,218,447 | 8/1980 | Isaac et al. . |
| 4,543,360 | 9/1985 | von Angerer et al. . |
| 4,734,434 | 3/1988 | Procaccini et al. . |
| 4,824,865 | 4/1989 | Bowser et al. . |
| 4,847,297 | 7/1989 | Chandra . |
| 5,061,700 | 10/1991 | Dow et al. . |
| 5,098,717 | 3/1992 | Blackman . |
| 5,576,346 | 11/1996 | Clemente et al. . |
| 5,593,682 | 1/1997 | Papas et al. . |
| 5,602,183 | 2/1997 | Martin et al. . |
| 5,646,190 | 7/1997 | Martin . |
| 5,648,380 | 7/1997 | Martin . |
| 5,663,208 | 9/1997 | Martin . |
| 5,702,688 | 12/1997 | Yu et al. . |
| 5,725,875 | 3/1998 | Noll et al. . |
| 5,747,462 | 5/1998 | Fuentes . |
| 5,789,399 | 8/1998 | Strube . |
| 5,798,093 | 8/1998 | Farrar et al. . |
| 5,863,938 | 1/1999 | Martin . |
| 5,874,479 | 2/1999 | Martin ..................................... 514/724 |
| 5,891,463 | 4/1999 | Bello et al. ............................. 424/449 |
| 5,945,398 | 8/1999 | Singh et al. ............................. 514/11 |
| 5,961,997 | 10/1999 | Swinehart ................................ 424/401 |

*Primary Examiner*—Marianne M. Cintins
*Assistant Examiner*—Vickie Kim
*Attorney, Agent, or Firm*—Michael Best & Friedrich LLP

[57] ABSTRACT

The present invention provides a method and composition for treating pruritus, and also psoriasis which includes applying a compound of formula (I) in a suitable formulation to the affected area. Compounds of formula (I) can also be formulated as a vaginal cream to inhibit viruses such as HIV, and possibly prevent the transmission of other sexually transmitted diseases.

6 Claims, No Drawings

TREATMENT OF PRURITUS

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF INVENTION

Pruritus is a condition involving localized or general itching. Although usually occurring in the skin, pruritus can also occur in non-cutaneous sites such as mucous membranes. A variety of causes for the condition of pruritus are known including external and endogenous causes, localized skin disorders and systemic diseases. For example, many systemic and skin diseases are accompanied by persistent or recurrent itch attacks. Itch can also be produced by a variety of chemical, mechanical, thermal and electrical stimuli.

Research into the causes of and treatment of pruritus has been limited by lack of animal models and low numbers of patients. Treatment involves diagnosis of the underlying condition that causes the pruritus and intervening therapeutically to alleviate that condition. For example, developments leading to antipruritic drugs have been, for the most part, a bonus of antiinflamatory drugs. Such treatments are not considered to be direct treatments of the pruritus and are of limited efficacy, only occasionally and indirectly relieving the itching. In many cases, however, either the underlying cause for the pruritic condition cannot be determined or cannot be eliminated. In such cases, the direct treatment of the pruritic condition is required.

Currently available treatment modalities for pruritus include nonspecific topical agents such as emollients and counterirritants, topical and oral drugs such as steroids, local anesthetics and antihistamines, and physical modalities such as ultraviolet phototherapy and thermal stimulation. Some of these treatments are effective in pruritic conditions of a particular etiology, while others may show general but nonspecific benefit. It is also known that although many corticosteroids, e.g., hydrocortisone, fluocinide, betamethasone valerate, fluocinolene acetonide, triamcinolone acetonide and others, have antiprutitic properties, prolonged use of such corticosteroids is associated with both cutaneous and systemic toxic side effects (e.g., fluid and electrolyte disturbances, impaired wound healing, musculoskeletal, gastrointestinal, neurological and endocrine disturbances) and their widespread use is limited without medical supervision. In any event, remission of the pruritus is often slow and frequently incomplete.

Nonspecific topical preparations can act as moisturizing lotions or creams or as oil-based ointments that are occlusive and serve to soften dry skin as well as provide a protective layer. While such preparations may have valuable moisturizing and skin softening properties, they also possess undesirable effects in that they generally impart to the skin an uncomfortable feeling of warmth in addition to a sticky, oily, greasy or waxy feel. More importantly, these materials alone have little effect, if any, on reducing itching.

Topical formulations containing pharmacologically active agents are often useful in particular pruritic conditions but many may not be generally useful in all pruritic conditions. For example, topical corticosteroids are not indicated for symptomatic treatment unless a steroid responsive disorder is diagnosed.

Thus, there is a continuing need for development of new and improved, nontoxic antipruritic agents that are effective in treating pruritus resulting from a wide variety of causes or that alleviate pruritus produced by causes different than those that can be treated by currently available agents.

BRIEF SUMMARY OF THE INVENTION

The present invention provides a method of treating pruritus which includes topically applying a compound of formula (I) described hereinafter in a mixture with a dermatologically acceptable vehicle. It has been found that compounds of formula (I) can be applied topically at pruritic sites and are surprisingly therapeutically effective such that the pruritus is rapidly and completely relieved.

The compound of formula (I) is preferably the compound of formula (II) described hereinafter, which is glyceryl triacetate or 1, 2, 3 propanetriol triacetate or, commonly, triacetin. Triacetin has been used as a pharmaceutical plasticizer (U.S. Pharmacopeia National Formulary 1075–76, 1492 (1985), as an antifungal drug and a fixative in perfumery (see, The Merck Index ($12^{th}$ ed.) p. 1636 (1996); U.S. Pat. No. 3,070,497 issued to Knight), listed as one of many general pharmaceutical carriers/diluents for primarily systemic administration of specific compounds (see, e.g., U.S. Pat. No. 4,543,360 issued to von Angerer et al.; U.S. Pat. No. 4,218,447 issued to Isaac et al.; U.S. Pat. No. 4,055,653 issued to Offermanns et al.; U.S. Pat. No. 4,847,297 issued to Chandra; U.S. Pat. No. 5,061,700 issued to Dow et al.), as an alkalinity reducing agent in permanent waving treatments for hair (see, e.g., U.S. Pat. No. 3,975,515 issued to Wajaroff et al.), and as an ingredient in a vaginal tampon (see, U.S. Pat. No. 3,091,241 issued to Kellett). It is noted that despite disclosure that triacetin is a general antifungal agent, a U.S. Food & Drug Administration Over-the-Counter Drug Review Panel has concluded that there is no evidence that triacetin is effective in any fungal disease other than the soggy toeweb form of athlete's foot. The OTC panel also concluded that triacetin was safe for topical use (see, Federal Register, vol. 47, 12553 (Mar. 23, 1982)). It has not heretofore been known that triacetin and compounds of formula (I) can be effectively used in the treatment of pruritic conditions.

The foregoing and other advantages of the present invention are realized in one aspect thereof in a method of treating pruritus which comprises applying a compound of formula (I) in an inert vehicle to the pruritically affected area.

In another aspect, the invention provides a method of treating pruritus which includes applying a composition to the pruritically affected area, which composition essentially consists of a pH modifying substance, self regulating at the molecular level, that stabilizes the desirable healthy skin pH, namely a compound of formula (I).

In a further aspect, the invention provides a topical antipruritic composition consisting of 5–100%, preferably 5–50% by weight of a compound of formula (I) and 0%–95% by weight a dermatologically acceptable vehicle.

In yet a further aspect, the invention provides a prodrug composition for treating pruritus which consists essentially of 5–100% by weight of a compound of formula (I) and 0%–95% by weight a dermatologically acceptable vehicle.

DETAILED DESCRIPTION OF THE INVENTION

The present invention relates to a method of treating pruritus which is highly effective in providing rapid and sustained relief. Accordingly, the present invention will now be described in detail with respect to such endeavors. Those skilled in the art will appreciate that such a description of the invention is meant to be exemplary only and should not be viewed as limitative of the full scope thereof.

The term "pruritus" is meant to refer to itching which can range from a mild sensation to an intense sensation of itching pain. The itching may accompany primary skin disease or may be a symptom of systemic disease— sometimes the only symptom. Skin diseases in which itching can be most severe include, among others, scabies, pediculosis, insect bites, urticaria, atopic dermititis, contact dermititis, lichen planus, miliaria and dermititis herpetiformis. Also, dry skin (especially in the elderly) is often a cause of severe generalized itching.

The present invention is suitably used for the relief of epidermal or dermal itching associated with any condition such as a systemic disease or allergy that affect epidermal and/or dermal nerve endings, an injury resulting in localized trauma affecting the epidermal or dermal nerve endings, or localized dermititis. In a preferred method, the invention includes a method of relief of pruritic symptoms associated with dermititis including actinic dermititis, contact dermititis such as an allergic dermititis or contact dermititis caused by irritating substances of plant, animal, mineral or synthetic origin.

The method of the present invention includes applying to an affected area an effective amount of a compound of formula (I):

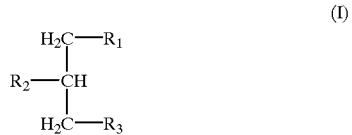

(I)

wherein $R_1$, $R_2$ and $R_3$ are each independently —$CH_3COO^-$ or H provided that $R_1$, $R_2$ and $R_3$ are not all H. When $R_1$ is —$CH_3COO^-$ and $R_2$ and $R_3$ are H, the compound of formula (I) is glyceryl monocetate or monacetin. When $R_1$ and $R_2$ are —$CH_3COO^-$ and $R_3$ is H, the compound of formula (I) is glyceryl diacetate or diacetin. When $R_1$, $R_2$ and $R_3$ are all —$CH_3COO^-$, the compound of formula (I) is glyceryl triacetate or triacetin. Triacetin or 1,2,3 propanetriol triacetate or glyceryl triacetate is given by formula (II):

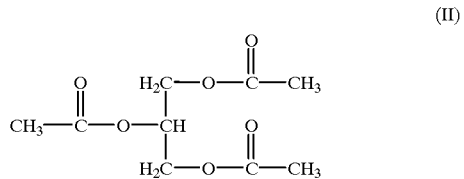

(II)

Compounds of formula (I) have not previously been recognized as a drug that undergoes biotransformation to exhibit a desired pharmacological effect i.e., it is, in effect, a prodrug. Compounds of formula (I) are readily broken down by enzymes, namely esterases, present in or on the skin, in mucus membranes and in body fluids, into glycerol (a skin protectant), acetate ion and hydrogen ion. The action of the esterases continues until the pH of the environment is changed to about 3.5 to 4.5 which is the normal range for healthy skin. At this pH level, the activity of the esterases is inhibited until the pH rises to the level where the esterases again become active. Also present in the skin and other bodily environments is a protease enzyme that signals the itch sensation. This protease is also pH sensitive in the same range, and it is believed that pH balance that is possible with application of compounds of formula (I) provides a dramatic and surprising effect on pruritus.

The compounds of formula (I) are commercially available. For example, triacetin is commercially available in USP grade from Eastman Chemical Company, Kingsport, Tenn. It is a colorless, somewhat oily liquid with a slight fatty odor with a density at 25° C. of 1.156 g/mL. It is prepared by acetylation of glycerol. Triacetin, diacetin and monacetin are soluble in water and miscible with alcohol, ether and chloroform.

For topical application, suitable viscous, semi-solid or solid forms can be employed which include a carrier compatible with topical application. Suitable formulations include, but are not limited to, solutions, suspensions, emulsions, creams, ointments, powders, liniments, salves, sprays, aerosols and gels. Preferably, compounds of formula (I), e.g., triacetin, are formulated as an ointment in which the vehicle is Aquaphor®, commercially available from Beiersdorf Inc., Norwalk, Conn., US. Aquaphor® is a composition of petrolatum, mineral oil, mineral wax and wool wax alcohol. Compounds of formula (I) are also suitably formulated as up to a 6% solution in water, and a 25% solution in 50% alcohol, suitably isopropyl alcohol.

Optionally, the skin treating compositions of the present invention may suitably include auxiliary agents such as plasticizing agents, preservatives, stabilizers, demulsifiers, wetting agents, opacifiers, surfactants, fragrances, sunscreens, antibiotics, insect repellents, preservatives, emollients, humectants, emulsifiers, thickeners, moisturizers, astringents, deodorants as well as other compatible materials which may be desired to enhance the properties of the compositions.

Other suitable emollient vehicles include hydrocarbon oils and waxes and volatile silicone fluids such a low molecular weight dimethyl siloxanes.

For topical treatment of pruritus, the concentration of compounds of formula (I) in a locally applied composition is about 5% to about 100% by weight, preferably about 5% to about 50% by weight, i.e., about 0.05 g/g to 0.5 g/g of composition, and most preferably, the concentration is about 20% by weight.

The compounds of formula (I), particularly, triacetin, have been found of value in the relief and treatment of pruritus due to leukoclastic vasculitis, macular lesion from drug allergies, skin conditions associated with renal disease, dry skin, dandruff, anal itch, poison ivy, poison oak, poison sumac, insect bites, vaginitis, bladder infection, diaper rash, cradle cap and eczema. Compounds of formula (I) may also be of value in prevention of sexually transmitted diseases, for example, when administered as a vaginal cream which can control and normalize vaginal acidity, maintain vaginal flora and may inhibit viruses present. Compounds of formula (I) are also of value in treating psoriatic lesions. Triacetin has been found to improve psoriatic lesions, applied as a topical, episodic treatment for psoriasis.

The skin treating compositions of the present invention when applied to the skin, e.g., up to four times per day as needed, provide reduction in and relief from itching within about 24–36 hours, and relief may even be evident after the first dose. For treatment of psoriasis, improvement is often seen within a day, with complete healing occurring within about 5 to 7 days.

The skin treating composition of the present invention is suitably formulated by simply mixing the compounds of formula (I) with the vehicle at room temperature. The composition is formulated to provide delivery of the antipruritic compound at a suitable rate and concentration. The composition may be in the form of any formulation that provides the compound as bioavailable to esterase action.

The following examples are intended to illustrate, but not limit, the scope of the invention. All parts and percentages in the examples are on a weight basis unless otherwise stated.

Medicament Preparations

EXAMPLE 1

An ointment was prepared by dissolving 20 g of triacetin in 80 g of Aquaphor® to yield a 20% by weight cosmposition.

EXAMPLE 2

A topical cream is prepared by dissolving 20 g of triacetin in 40 g of mineral oil and 20 g of self-emulsifying beeswax. The mixture is heated to liquify. After the addition of 20 mL of hot water, the mixture is mixed well. The resulting cream contains approximately 20 g of triacetin per 100 gram of cream.

EXAMPLE 3

A dermatological lotion is prepared by dissolving 20 g of triacetin in 80 g of dry propylene glycol. The resulting lotion contains about 20 g of triacetin per 100 g of lotion.

EXAMPLE 4

An ointment is prepared according to Example 1 by dissolving monacetin.

EXAMPLE 5

An ointment is prepared according to Example 1 by dissolving diacetin.

Dermatological Testing

EXAMPLE 6

Treatment of Pruritus

Compositions of triacetin were evaluated for therapeutic efficacy of the composition in the topical treatment of pruritus. The skin treating composition evaluated was the ointment composition prepared in Example 1. The patients were treated on an out-patient basis. The patients were instructed to apply the composition up to four times per day as needed.

More than 100 subjects who presented with pruritic conditions applied the ointment to the pruritic area up to 4 times per day as needed. Patients were asked to note the time within which itching was relieved and when the symptoms wholly disappeared and reported same to a physician. 90% of the patients reported relief from itching within 24–36 hours, and 75% reported that within about 48 hours of additional treatment, the symptoms essentially disappeared.

EXAMPLE 7

Treatment of Psoriasis

Eight patients who presented with psoriatic lesions were treated with the ointment of Example 1 on an out-patient basis. The ointment of Example 1 was applied to the psoriatic lesions up to four times per day. All patients reported to a physician improvement of the lesions within about a day of application, and healing within about 5–7 days.

In summary, the present invention provides a method and composition for treating pruritus, and also psoriasis, which includes applying compounds of formula (I) in a suitable formulation to the affected area. Compounds of formula (I) can also be formulated as a vaginal cream that may be of value for inhibiting viruses such as HIV.

Many variations will suggest themselves to those skilled in the art in light of the detailed description. All such modifications and variations are within the full intended scope of the appended claims.

What is claimed is:

1. A method of treating pruritus in a human or other mammal comprising administering to the human or mammal afflicted therewith a topical composition consisting essentially of an antipruritically effective amount of a compound of formula (I)

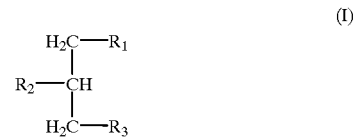

wherein $R_1$, $R_2$ and $R_3$ are each independently —$CH_3COO^-$ or H provided that $R_1$, $R_2$ and $R_3$ are not all H, and an inert vehicle to a pruritically affected area.

2. The method of claim 1 where the compound of formula (I) is triacetin.

3. A method of treating pruritus comprising administering topically to a human or other mammal in need thereof an amount of a composition consisting essentially of a pH modifying substance and a dermatologically acceptable vehicle, said amount sufficient to normalize skin pH, said substance being a compound of formula (I)

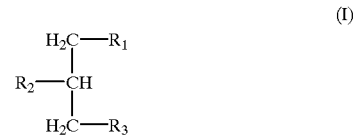

wherein $R_1$, $R_2$ and $R_3$ are each independently —$CH_3COO^-$ or H provided that $R_1$, $R_2$ and $R_3$ are not all H.

4. The method of claim 3 wherein the compound of formula (I) is triacetin.

5. A method for alleviating psoriasis in a human or other mammal comprising applying to the skin of a human or other mammal in need thereof an effective amount of a composition consisting essentially of a compound of formula (I)

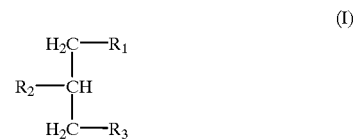

wherein $R_1$, $R_2$ and $R_3$ are each independently —$CH_3COO^-$ or H provided that $R_1$, $R_2$ and $R_3$ are not all H, and a dermatologically acceptable carrier.

6. The method of claim 5 wherein the compound of formula (I) is triacetin.

* * * * *